United States Patent [19]

Schoeff et al.

[11] Patent Number: 4,996,057

[45] Date of Patent: Feb. 26, 1991

[54] COMPOSITION FOR LOCALLY TREATING THE EPIDERMIS, ESPECIALLY THE SCALP

[75] Inventors: Nadine Schoeff, 12, Boulevard d'Andilly "Les Atlantes", 95160 Montmorency; Jean-Pierre Poujol, deceased, late of Saint-Owen, both of France, by Raymonde Poujol

[73] Assignee: Nadine Schoeff, Montmorency, France

[21] Appl. No.: 328,221

[22] PCT Filed: Mar. 21, 1988

[86] PCT No.: PCT/FR88/00147

§ 371 Date: Jan. 24, 1989

§ 102(e) Date: Jan. 24, 1989

[87] PCT Pub. No.: WO88/07363

PCT Pub. Date: Oct. 6, 1988

[30] Foreign Application Priority Data

Apr. 3, 1987 [FR] France ................................ 87 04737

[51] Int. Cl.$^5$ ................................................ A61K 7/06
[52] U.S. Cl. ........................................ 424/451; 424/70; 424/583; 514/648; 514/880; 514/881
[58] Field of Search ........................... 424/70, 95, 105; 514/648, 880, 881

[56] References Cited

U.S. PATENT DOCUMENTS

| | | | |
|---|---|---|---|
| 4,193,992 | 3/1980 | Fontaine | 424/105 |
| 4,359,468 | 11/1982 | Freter et al. | 546/199 |
| 4,542,012 | 9/1985 | Dell | 424/78 |
| 4,791,217 | 12/1988 | Robert et al. | 560/55 |
| 4,812,573 | 3/1989 | Durant et al. | 514/310 |
| 4,835,161 | 5/1989 | Janssens et al. | 514/303 |

Primary Examiner—Thurman K. Page
Assistant Examiner—Amy Hulina
Attorney, Agent, or Firm—Larson and Taylor

[57] ABSTRACT

The object of the invention is a composition for the local treatment of the epidermis comprising at least two active constituents, characterized in that one of these constituents is a product resulting from the condensation of N-methyl-p-methoxyphenethylamine with formaldehyde or product of the aromatic polyamine-type. It particularly relates to a composition for treating the scalp, particularly for treating alopeciae and alopecia aerata or pelada comprising, as second active constituent, a placental extract containing proteinic compounds and sulfurized amino acids. Application to the treatment of the epidermis, particularly of the scalp.

6 Claims, No Drawings

COMPOSITION FOR LOCALLY TREATING THE EPIDERMIS, ESPECIALLY THE SCALP

The invention relates to compositions for locally treating the epidermis.

More specifically, it concerns a composition intended for the local treatment of the epidermis, especially of the scalp, containing at least one principle active in the treatment considered and, as chemical mediator inducing the response of the receptors of said principle, at least one product resulting from the condensation of N-methyl-p-methoxyphenethylamine with formaldehyde.

The products of this type have as general formula $(C_{11}H_{15}NO)_n$, n most frequently representing an integer from 2 to 4.

It would appear that these products result from the chaining of units of the following formula:

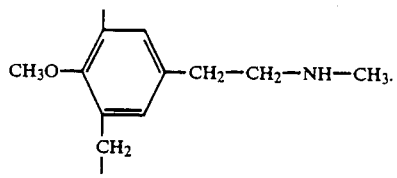

A product apparently consisting of a mixture of di-, tri- and tetramers of this unit is marketed by the SIGMA Company, P.B. 14508, Saint Louis, MO 63178, U.S.A. under the trade name "Compound 48/80".

This product also known under the name of "aromatic polyamine", is to be found under the form of hydrochloride of the general formula $(C_{11}H_{15}NO, HCl)_n$, with a molecular weight $(213,7)n$.

This is a water-soluble (50 mg/ml) white powder.

The aromatic polyamine has been known since the 50s as a histamine releaser and is used in allergology as reference product in skin tests.

So far, the products of this type have never been proposed for use in prophylactic or curative compositions.

In a surprising and unexpected way it has now been found that the products resulting from the condensation of N-methyl-p-methoxyphenethylamine with formaldehyde such as defined above and hereinafter referred to as "products of the aromatic polyamine-type" can advantageously be used in compositions for the local treatment of the epidermis, especially of the scalp.

More specifically, it has been found that the combined use of the products of the aromatic polyamine type with principles alledgedly active in the epidermic region, increases in a considerable and unexpected way the activity of the latter, and this without undesired side effects while maintaining a localized action.

Generally speaking, the object of the invention is therefore a composition for the local treatment of the epidermis comprising at least two active constituents characterized in that one of these constituents is a product resulting from the condensation of N-methyl-p-methoxyphenethylamine with formaldehyde or product of the aromatic polyamine-type.

The other active constituent is a compound or mixture of compounds known to be more or less active in the application considered.

The composition according to the invention can be adapted to the local treatment of the epidermis on any part of the body, where a cell regeneration is necessary.

According to a particularly advantageous and preferred embodiment, the composition according to the invention is intended for the scalp, in particular for treating alopeciae and alopecia aerata or pelada.

Thus, according to a particular embodiment, the object of the invention is a composition for treating the scalp, particularly for treating alopeciae and alopecia aerata or pelada, characterized in that it includes an efficient amount of proteinic compounds and a non-allergenic amount, although capable of activating the response of the hair follicles, of at least one product resulting from the condensation of N-methyl-p-methoxyphenethylamine with formaldehyde.

According to a preferred embodiment, this composition also contains sulfurized amino acids.

According to an advantageous embodiment of the present invention, the proteinic compounds and as the case may be the sulfurized amino acids are introduced under the form of organic extracts from human or animal origin. They may also be introduced under the form of a mixture of proteins and, if required, of sulfurized amino acids, obtained for example by synthesis or extraction and advantageously used in the proportions observed in the organic extracts.

A particularly suitable organic extract to be used in connection with the present invention is for example the lyophilized "amino proteinic complex" resulting from the mincing or grinding of human placental tissue marketed under the trademark PHYLDERM POUDRE by the Etablissements Gattefossé, 36 chemin de Genas, 69804 Saint Priest (France). Another extract of this type is the one sold by the Société Organotechnie, 27 avenue Jean Mermoz, 93120 La Courneuve (France).

Generally, the composition according to the invention can be formulated under any form suitable for the local application or for the intradermic administration, in the presence of a physiologically compatible excipient.

Thus, for the local application, the composition according to the invention may be presented under the form of an aqueous solution, preferably in demineralized water, or under the form of a cream.

For the intradermic application (ionization), the composition according to the invention can be presented under the form of an aqueous solution in demineralized water, having a pH close to 7 and being conditioned in ampullae, for example of 1 to 10 ml, particularly of 3 ml.

For the intradermic administration, the same type of ampullae is used, however sterilized.

According to a preferred embodiment, the object of the invention is an aqueous solution or lotion for the treatment of the scalp, particularly for the treatment of alopeciae and alopecia aerata or pelada, characterized in that it includes from $10^{-3}$ to 1 mg/ml of product of the aromatic polyamine-type and from 0.1 to 10 mg/ml of mixture of proteinic compounds and of sulfurized amino acids under the form of lyophilized placental extract.

According to another preferred embodiment, the object of the invention is an aqueous solution for the intradermic application with ionization, in the treatment of the scalp, particularly in the treatment of alopeciae and alopecia aerata or pelada, conditioned preferably under the form of ampullae, characterized in that it includes from $10^{-3}$ to 1 mg/ml of product of the aromatic polyamine-type and from 0.1 to 10 mg/ml of mixture of proteinic compounds and of sulfurized amino acids under the form of lyophilized placental extract.

According to another preferred embodiment, the object of the invention is a sterile aqueous solution for the intradermic administration in the treatment of the scalp, particularly in the treatment of alopeciae and alopecia aerata or pelada, conditioned preferably under the form of ampullae, characterized in that it includes from $10^{-3}$ to $10^{-1}$ mg/ml of product of the aromatic polyamine-type and from 0.05 to 5 g/ml of mixture of proteinic compounds and of sulfurized amino acids under the form of lyophilized placental extract.

According to still another preferred embodiment, the object of the invention is a cream for the treatment of the scalp, particularly for the treatment of alopeciae and alopecia aerata or pelada, characterized in that it includes from $10^{-3}$ to 1 mg/g of product of the aromatic polyamine-type and from 1 to 15 mg/g of mixture of proteinic compunds and of sulfurized amino acids under the form of lyophilized placental extract.

The excipient of the cream may consist of any excipient or mixture of excipients used in the creams intended for pharmaceutical or cosmetic applications and compatible with the active principles of the composition according to the invention, particularly in the presence of an emulsifying agent such as the one sold under the trademark Emulgade FS by the Henkel Company.

The cream may also contain other excipients such as beeswax or a polyalcohol such as glycerol.

The pH of the aqueous solutions is advantageously adjusted close to 7 and the pH of the cream close to 5.

In order to reduce the pH, there can be used any acid pharmacologically acceptable and compatible with the constituents of the solution or of the cream, for example citric acid.

In order to increase the pH, there can be used any base pharmacologically acceptable and compatible with the constituents of the solution or of the cream, for example triethanolamine.

All these products, and particularly the creams, may as the case may be contain one or several preservatives such as methylparaben.

The purpose of the following non-limiting examples is to yield a better explanation of the invention.

EXAMPLE 1

Lotion for the local application onto the scalp 100 l of solution contain:
product of the aromatic polyamine-type sold by the SIGMA Company under the trade name "Compound 48/80": 10 g
lyophilized "amino proteinic complex" resulting from the mincing or grinding operation of human placental tissue, in powder, sold under the trademark PHYLDERM by Société Gattefossé: 400 g
methylparaben: 3 l
as the case may be citric acid or triethanolamine q.s. pH close to 7
demineralized water: q.s. 100 l.

EXAMPLE 2

Ampullae for the intradermic application onto the scalp with ionization 100 ml of the solution contain:
product of the aromatic polyamine-type sold by the SIGMA Company under the trade name "Compound 48/80": 10 mg
lyophilized "amino proteinic complex" resulting from the mincing or grinding operation of human placental tissue, in powder, sold under the trademark PHYLDERM by Société Gattefossé: 400 g
methylparaben: 3 ml
as the case may be citric acid or triethanolamine q.s. pH close to 7.

The solution is conditioned in plastic 3 ml-ampullae with an applicator tube.

EXAMPLE 3

Ampullae for the intradermic administration into the scalp 100 l of solution contain:
product of the aromatic polyamine-type sold by the SIGMA Company under the trade name "Compound 48/80": 1 mg lyophilized "amino proteinic complex" resulting from the mincing or grinding operation of human placental tissue, in powder, sold under the trademark PHYLDERM by Société Gattefossé: 100 g
as the case may be citric acid or triethanolamine q.s. pH close to 7.

The solution is conditioned in glass 3 ml-ampullae which are sealed and sterilized.

EXAMPLE 4

Cream for the application onto the scalp 100 g of cream contain:

| | |
|---|---|
| "Compound 48/80" of SIGMA: | 10 mg |
| PHYLDERM POUDRE of GATTEFOSSE: | 800 mg |
| Stearic acid: | 4 g |
| Cetylic alcohol: | 4 g |
| Emulgade ® FS: | 8 g |
| Lanolin: | 6 g |
| Beeswax: | 15 g |
| Vaseline oil: | 20 g |
| Demineralized water: | qs 100 g |

The active principles (Compounds 48/80 and PHYLDERM) are dissolved in demineralized water. Besides, the other constituents of the cream are mixed, the mixture is heated and allowed to cool under a slow stirring down to 25° C. The aqueous phase prepared separately is then incorporated and, if needed, the pH is adjusted as stated above.

APPLICATIONS OF THE COMPOSITIONS ACCORDING TO THE INVENTION

EXAMPLE 5

Application of the Lotion of Example 1

This Lotion can be used, in particular when treating alopecia, in local application.

The daily dose is approximately 50 drops to be distributed over the bald patch or region of alopecia.

EXAMPLE 6

Treatment by Ionization

Ampullae of Example 2 are advantageously used by having them enter the scalp under ionization, within 20 minutes. This treatment is conducted at a rate of once to twice a week by gradually increasing the dose every second to third week, viz. according to the pattern 1 ml, 1.5 ml, 2 ml, 2.5 ml, 3 ml.

EXAMPLE 7

Use of the Cream of Example 4 for the Puvatherapy

The application is made as a thin layer 10 minutes following the end of ionization.

The layer is all the more so thin since the sessions take place at increasingly frequent intervals, however its thickness essentially depends on the cutaneous reactivity of the patient.

In the case of alopecia aerata or pelada, this application generally takes place twice a week, whereas in the case of alopecia one application once a week generally proves sufficient.

EXAMPLE 8

Application by Intradermic Administration

The injectable ampullae of Example 3 are used.

The determination of the dose of the chemical mediator depends upon the cutaneous reactivity and age of the patient. It has been observed that regardless of the dose used, the extent of reaction edema decreases as the age increases.

It could thus statistically be ascertained that the reactivity is as follows:
maximum from 10 to 29 years,
intermediate from 30 to 49 years,
minimum above 50 years.

An overall study performed on 70 patients showed that the reaction percentage is generally the highest with a dilution of $10^{-2}$ mg/ml.

CLINICAL AND PARACLINICAL EXPERIMENTS

I, Treatment of Alopecia

The combination aromatic polyamine plus proteinic complex of Examples 1 and 2 has been experimented on 2000 patients suffering from androgenetic alopecia.

These were male patients suffering from an androgenetic alopecia of types 3 and 4 according to the Hamilton table. In each case, the composition was applied in the manner described above.

The cutaneous reaction proved excellent in 95% of the cases and allowed the performance of a regular treatment in 100% of the cases.

Results

1. Action on hair loss

After one month of treatment: decrease of the hair loss in 55% of the cases;

After two months of treatment: stop of the hair loss in 75% of the cases;

After three months of treatment: stop of the hair loss in 85% of the cases.

2. Regrowth

It can be verified from the fourth month onwards it is only obtained on hair follicles possessing still living germinative cells. It is scarce in the temporal gulfs, since the germinative cells are seldom living in said areas for the types 3 and 4 of baldness according to the table of Hamilton.

With the female patient, the regrowth remains possible in 80% of the cases.

The bald area fills in starting from its periphery, the last falling hair being the first to be replaced.

In 70% of the cases, regrown hair can be observed over the whole bald area after 6 to 7 months of treatment.

The paraclinical examination (study by trichogram) makes it possible to corroborate the favorable tendency verified by the clinical examination.

The evaluations are made on day 0 and on day 6 months, by counting the number of hair in different phases (anagen, catagen, telogen, dystrophy I and dystrophy II).

Based on these criteria, it is ascertained that the following results are obtained:

in 55% of the cases a normalization of the pilar formula;

in 35% of the cases an improvement without normalization of the pilar formula; and in 10% of the cases, no change in the pilar formula.

II. Treatment of Alopecia Aerata or Pelada

In the case of alopecia aerata or pelada, the composition of Example 4 is used in local application, over the peladic area.

A satisfactory result is obtained (regrowth of the hair) on localized pelada patches, in 100% of the cases, after 6 to 12 months of treatment (whatever the number of pelada patches and their localization may be).

In the case of hair destroying pelada, pending experiments yield results which seem to be satisfactory.

III. Clinical Experiment Pertaining to the Tenacity of the Regrown Hair

The pharmaceutical composition according to the invention, in particular the composition of Examples 1 to 4, enables the hair to grow from a living germinative cell incapable of ensuring its function alone. The composition according to the invention restores this function thanks to the combined action of its components.

Clinical experiments over seven years have made it possible to ascertain the preservation of the acquired regrowth in 80% of the cases jointly with a backup treatment of 1 to 2 treatment courses annually.

The following table shows the results of a comparative study between the results obtained over a period of six months with a solution of the aromatic polymine alone, a solution of the proteinic complex alone and the composition according to the invention (lotion of Example 1).

TABLE

| | ACTION ON REGROWTH | | | |
|---|---|---|---|---|
| | No change | Beginning of regrowth as down and small thin hair | Marked regrowth + decrease in diameter of alopecia areas | Very substantial regrowth and very marked decrease of alopecia areas |
| aromatic polyamine alone | 80% | 20% do not hold | 0 | 0 |
| proteinic | 40% | 60% | 0 | 0 |

TABLE-continued

| | ACTION ON REGROWTH | | | |
|---|---|---|---|---|
| | No change | Beginning of regrowth as down and small thin hair | Marked regrowth + decrease in diameter of alopecia areas | Very substantial regrowth and very marked decrease of alopecia areas |
| complex alone | | do not hold | | |
| proteinic complex + aromatic polyamine | 5% | 7% | 38% | 50% |

From the study of this table it can be verified that the polyamine used alone brings about a slight beginning of hair regrowth under the form of down and of small thin hair, the proteinic complex permits an improved beginning of regrowth, however without any marked regrowth nor substantial regrowth, whereas the composition according to the invention yields very good results, viz. in particular a very substantial regrowth and a very marked decrease of alopecia areas for 50% of the patients, whereas the regrowth is marked in 38% of the cases.

It should be noted that as a general rule the composition according to the invention produces its effects on the area of application, without spreading or scattering beyond this area. The composition according to the invention therefore has a strictly localized activity on the area of application either by local or subcutaneous way.

STUDY ON TOXICITY

The composition according to the invention does not cause any tissue damage and has a uniform action when applied onto an isolated organ.

The evaluation of primary cutaneous irratation and ocular irritation in the rabbit, and the innocuousness test by oral administration to the rat were carried out in compliance with the methods published in the Journal Officiel de la République Française on Feb. 21, 1982 and Sept. 21, 1984, in agreement with the Recommendat ons for Good Laboratory Practice (France, Department of Health—Instructions 1065 of May 31, 1983).

The studies were carried out at the international center for toxicity at Meserey 27005 Evreux—France.

EXPERIMENT PROCEDURES

Primary Cutaneous Irritation in the Rabbit

It was evaluated following the topical application of 0.5 ml of the lotion of Example 1 onto the scarified skin and the non-scarified skin of 6 New Zealand male rabbits (animals received from the breeding center of Abbaye de Bellefontaine 49122 Begrolles en Mauges—France) having an average weight of 2.5 kg.

The right flank of the animals was scarified (three parallel scarifications over a length of about 2.5 cm, spaced at 0.5 cm); the scarifications of the epidermis were carried out by means of a "vaccinostyle" or small vaccine lancet, without reaching the dermis.

0.25 ml of the composition according to the invention were directly applied onto an area of 6 cm² then covered with a square of Codex hydrophilic gauze. A collar had been fastened around the animals' neck in order to prevent them from licking themselves.

The product and squares of gauze were maintained in contact with the skin by means of an occlusive dressing. 24 hours after the application, the dressings were removed. The period during which the animals were subjected to observation amounted to 3 days.

No erythema could be observed. The product is therefore considered as being non-irritating.

Ocular Irritation in the Rabbit

This irritation was evaluated after instilling 0.1 ml of the lotion of Example 1 into the conjunctival pouch of six New Zealand male rabbits having a weight of 2.5 kg.

Experiment Procedure 0.1 ml of the lotion according to the invention is instilled into the lower left conjunctival pouch of e ch rabbit, by means of a syringe. The eyelids are maintained in contact for a few seconds in order to avoid any loss of the substance. The right eye does not receive any product and is used as control. In view of the treatment and for an hour, the animals are placed in a plastic immobilizing container. The instillation is followed with a period of observation of the animals of 7 days.

No ocular reaction is observed.

Test of Innocuousness by Oral Administration to the Rat

This test was performed according to the specifications set forth in the standard OCDE No. 401 concerning the study of acute toxicity of chemical products administered orally.

For the study, were used rats of the Sprague-Dawley strain: CD(SD)BR which is the recommended species for this type of experiment. These rats came from the breeding center Charles River France (76410 Saint-Aubin lès Elbeuf—France).

At the beginning of the experiment their weight amounted to 110 to 160 g.

A single volume of 5 ml per kg of the lotion of Example 1 was administered by means of a forcible-feeding canula to each animal of a group of ten animals (5 males and 5 females). The record of clinical signs was performed at least once a day for the following 14 days.

No death nor any sign of toxicity was recorded throughout the study.

The oral administration of the composition of Example 1 according to the invention does not therefore produce any sign of toxicity for a dose of 5 ml per kg.

I claim:

1. A composition for the local treatment of the scalp of a subject comprising from 0.1 to 10 mg/ml of proteinic compounds from human placental tissue and from $10^{-3}$ to 1 mg/ml of a condensation product of N-methyl-p-methoxyphenethylamine with formaldehyde.

2. A composition according to claim 1 wherein the condensation product has the general formula $(C_{11}H_{15}NO)_n$ wherein n is an integer of 2 to 4.

3. A composition according to claim 1 wherein the proteinic compounds include sulfurized amino acids.

4. A composition according to claim 3 wherein the mixture of proteinic compounds and sulfurized amino acid are in the form of lyophilized placental extract.

5. A composition according to claim 1 in the form of an aqueous solution for intradermic application with ionization wherein the condensation product comprises from $10^{-3}$ to 1 mg/ml of product and the mixture of proteinic compounds and sulfurized amino acids from 0.05 to 5 g/ml of product.

6. A composition according to claim 4 in the form of a cream and wherein the condensation product comprises from $10^{-3}$ to 1 mgl/g of product and the mixture of proteinic compounds and sulfurized amino acids from 1 to 15 mg/g of product.

* * * * *